(12) United States Patent
Brady

(10) Patent No.: US 7,498,567 B2
(45) Date of Patent: Mar. 3, 2009

(54) OPTICAL WELLBORE FLUID CHARACTERISTIC SENSOR

(75) Inventor: Dominic Brady, Freemantle (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/767,487

(22) Filed: Jun. 23, 2007

(65) Prior Publication Data

US 2008/0314138 A1 Dec. 25, 2008

(51) Int. Cl.
*G01V 5/04* (2006.01)
(52) U.S. Cl. .................................................. 250/256
(58) Field of Classification Search ................ 250/256
See application file for complete search history.

(56) References Cited

U.S. PATENT DOCUMENTS

| | | | |
|---|---|---|---|
| 5,956,132 A * | 9/1999 | Donzier ..................... 356/133 |
| 6,023,340 A | 2/2000 | Wu et al. |
| 6,075,611 A | 6/2000 | Dussan et al. |
| 6,216,532 B1 | 4/2001 | Stephenson et al. |
| 6,388,251 B1 | 5/2002 | Papanyan |
| 6,768,105 B2 * | 7/2004 | Mullins et al. ............ 250/269.1 |
| 6,828,547 B2 * | 12/2004 | Tubel et al. ............. 250/227.14 |
| 6,927,846 B2 | 8/2005 | Smith et al. |
| 6,939,717 B2 | 9/2005 | Jiang et al. |
| 7,099,015 B2 | 8/2006 | Melnyk |
| 7,142,306 B2 | 11/2006 | Wu et al. |
| 7,255,173 B2 * | 8/2007 | Hosie et al. .............. 166/332.8 |
| 2005/0269499 A1 * | 12/2005 | Jones et al. .............. 250/269.1 |
| 2008/0043242 A1 * | 2/2008 | Emmerson et al. .......... 356/477 |

FOREIGN PATENT DOCUMENTS

| | | |
|---|---|---|
| GB | 2391939 A | 2/2004 |
| WO | 2005116388 A1 | 12/2005 |

\* cited by examiner

*Primary Examiner*—David P Porta
*Assistant Examiner*—Marcus H Taningco
(74) *Attorney, Agent, or Firm*—Winstead PC; Daryl R. Wright; James L. Kurka

(57) ABSTRACT

Evanescent waveguide sensors for measuring and determining the composition of wellbore fluids in situ are provided. The waveguides are provided on substrates have a thickness and strength sufficient to withstand wellbore pressures and a sufficient surface area to allow for broad range measuring of the wellbore characteristics. The optical sensors facilitate determination of the wellbore fluid composition without requiring in-tool sampling of the wellbore fluid.

18 Claims, 3 Drawing Sheets

OPTICAL WELLBORE FLUID CHARACTERISTIC SENSOR

FIELD OF THE INVENTION

The present invention relates in general to downhole wellbore logging devices and methods, and more particularly, to fiber optic sensors for measuring wellbore fluid characteristics in situ.

BACKGROUND

In wellbore operations it is often desirable to identify characteristics, such as the composition, of the wellbore fluid at identifiable locations in the wellbore. For example, in some circumstances it may be desirable to identify at what location in the wellbore that water, gas, or oil is entering from the surrounding formation. It may further be a desire to identify the presence of hydrogen sulfide or carbon dioxide.

It is a desire of the present invention to provide methods and apparatus for determining the composition and/or characteristics of wellbore fluids in the wellbore. It is a still further desire to provide optical fiber sensors for determining wellbore fluid characteristics. It is a still further desire to provide optical sensors and methods for determining the chemical composition of a wellbore fluid, in the wellbore, without requiring in-tool fluid sampling.

SUMMARY OF THE INVENTION

In view of the foregoing and other considerations, the present invention relates to determining the composition of wellbore fluids using optical sensors.

In an example of an optical apparatus for investigating wellbore fluids of the present invention, the apparatus includes an optical sensor having a waveguide formed on the surface of a substrate; a portion of the waveguide is open to the surrounding environment to emit an evanescent sensing field therein. The substrate has a thickness sufficient to withstand the pressures encountered in wellbores. More than one waveguide, or discreet sensor may be formed on the substrate.

An optical system includes one or more optical sensors carried by a wellbore tool. The tool may be a logging tool or drilling tool. The tool may carry one or more optical sensors. Multiple sensors may be formed on a single substrate. Desirably the optical sensor system of the present invention provides an economical, rugged optical sensor system that can determine the composition of the wellbore fluid, as well as other characteristics, without in-tool sampling of the fluid.

BRIEF DESCRIPTION OF THE DRAWINGS

The foregoing and other features and aspects of the present invention will be best understood with reference to the following detailed description of a specific embodiment of the invention, when read in conjunction with the accompanying drawings, wherein.

DETAILED DESCRIPTION

Figure 1:
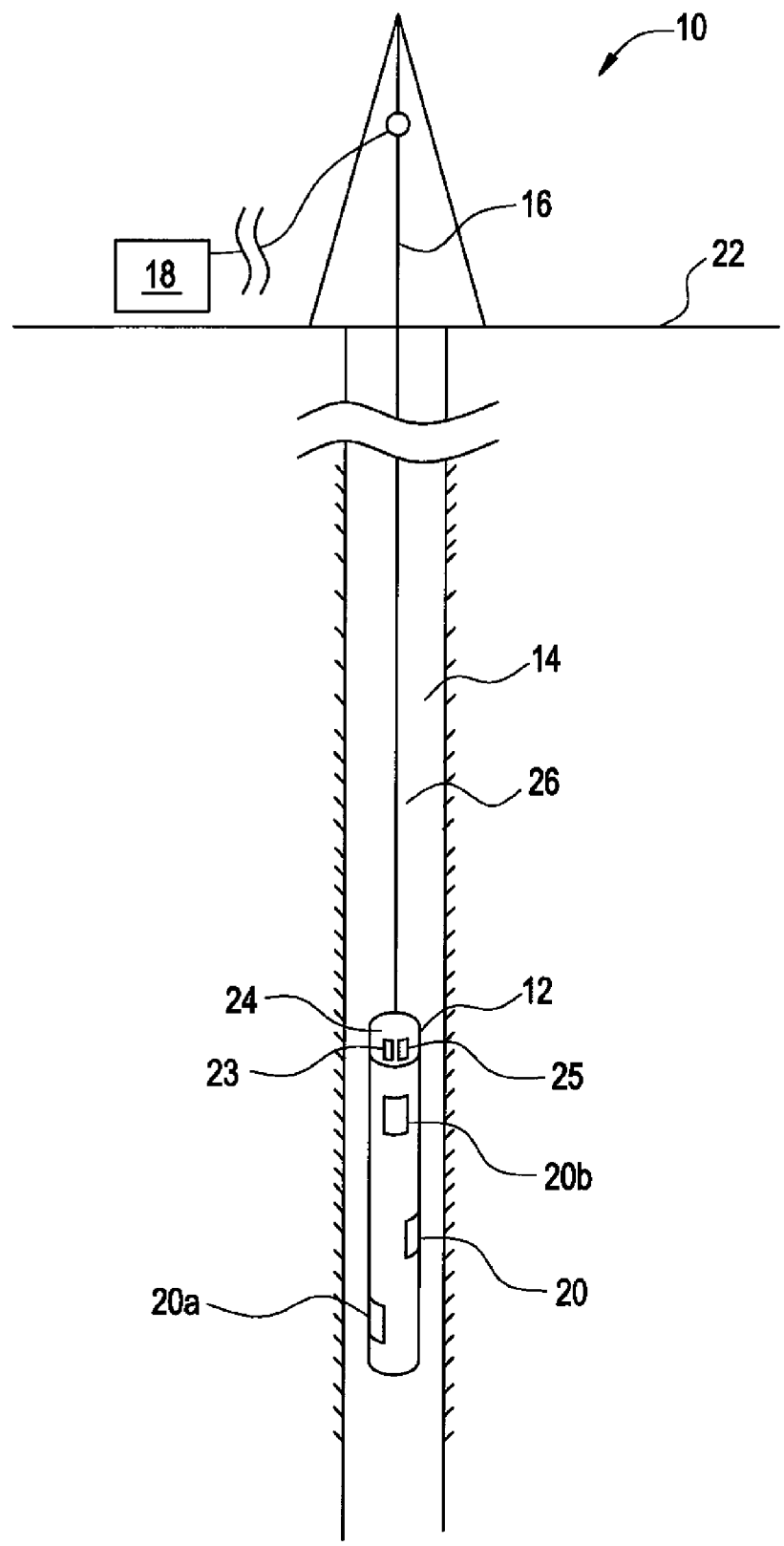
FIG. 1 is a wellbore schematic wherein an optical sensor system of the present invention is deployed.

Refer now to the drawings wherein depicted elements are not necessarily shown to scale and wherein like or similar elements are designated by the same reference numeral through the several views.

As used herein, the terms "up" and "down"; "upper" and "lower"; and other like terms indicating relative positions to a given point or element are utilized to more clearly describe some elements of the embodiments of the invention. Commonly, these terms relate to a reference point as the surface from which drilling operations are initiated as being the top point and the total depth of the well being the lowest point.

Referring now to FIG. 1, an optical borehole composition sensor system of the present invention, generally denoted by the numeral 10, is illustrated. A tool 12 is suspended in a well 14 or borehole by a conveyance 16. In the illustrated example, tool 12 is a production logging tool and conveyance 16 is a cable. Cable 16 may include conductors (not shown), which may be electrical and/or optical, for communicating with data processing equipment 18. Tool 12 may be utilized with or incorporated into a logging or measurement while drilling tool and conveyed by tubing or drill pipe.

Tool 12 includes one or more optical sensors 20 for detecting and measuring various characteristics of the contents of the wellbore such as, but not limited to, water cut of the wellbore fluid 26, gas holdup, oil composition, carbon dioxide content, hydrogen sulfide detection, temperature and pressure. An optical (light) source 23 and detection equipment 25 are in operational connection with the one or more optical sensors 20. The light source 23 and detection equipment 25 may be located in various locations such as the surface 22 or in the electronics housing 24 of tool 12.

Tool 12 includes one or more evanescent waveguide sensors 20 that are operational in the harsh environment of wellbores. Evanescent sensors 20 include reflectance, transmission sensors 20a (FIG. 2) and refractive index sensors 20b (FIG. 3). Note that sensors 20 are optical fiber sensors and therefore are very small in relation to tool 12. As noted with reference to FIG. 1, one or more sensors 20 may be carried by tool 12. If tool 12 includes a plurality of sensors 20, the sensors may be positioned proximate to one another or scattered along tool 12. It should further be recognized that sensors 20 may be positioned in wellbore 14 in various manners including the logging tool example described herein.

Figure 2:
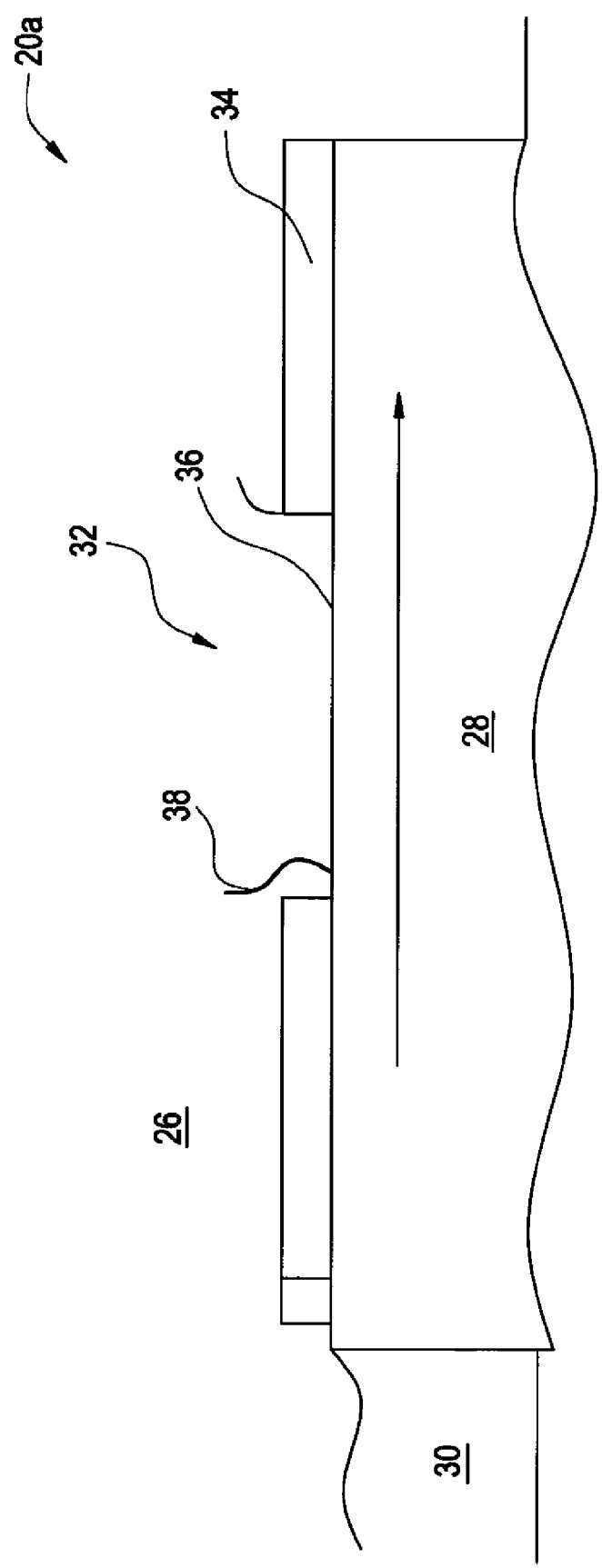
FIG. 2 is a side view of an example of a reflectance optical sensor of the present invention.
Figure 3:
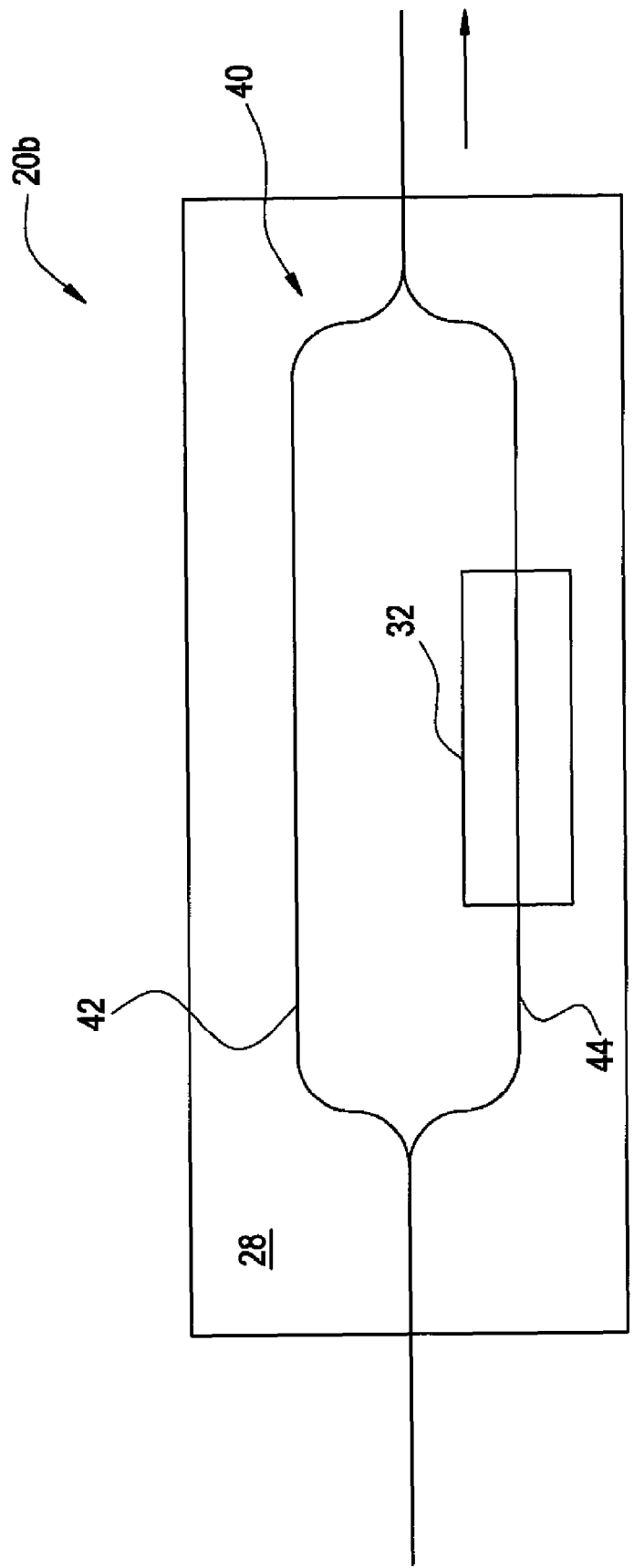
FIG. 3 is a plan view of a refractive index optical sensor of the present invention.

Sensors 20 include waveguides that are fabricated on the surface of a substrate 28 (FIGS. 2, 3). The waveguides may be fabricated using in-diffusion or ion implantation and both processes may be based on reproducible and standard photo-lithographical/planar processing. These methods facilitate the accurate definition of both the waveguide path and the size of the windows 32 (FIGS. 2, 3) to specify the properties of the sensor.

Various materials such as sapphire, silicon, silica and diamond may be utilized for the substrate. Sapphire provides benefits that are desirable for utilization in wellbores. Some of the benefits of sapphire crystals include low cost and availability in relatively large sizes. Size of the substrate is important for various reasons. For example, the thickness of substrate 28 must be sufficient to withstand the pressures, in particular the pressure differential across substrate 28, encountered in wellbores. Sapphire substrates can readily be obtained in thicknesses of 6 mm, providing suitable strength for many wellbore applications. Although substrate 28 is illustrated and described in terms of planar configurations, cylindrical or hemispherical sapphire substrates 28 may be utilize in particular for high pressure and/or high temperature wells. Additionally, sapphire substrates 28 are available with large surface areas (for example, diameters of 25 mm) providing for the placement of a number of discreet sensors on each substrate.

Refer now to FIG. 2 wherein a side view of a reflectance sensor 20a is illustrated. A sapphire substrate 28 is provided in connection with an optic fiber 30. A window 32 is formed through the covering or overclad 34 exposing a portion of the surface 36 of substrate 28 on which the waveguide (40, FIG.

3) is formed. Window 32 exposes fluid 26 directly to the evanescent field and forming a sensing field 38.

Sensor 20a measures the spectral content of the waveguide transmission. Fluid 26 in contact with the evanescent field of the waveguide will have a characteristic absorption fingerprint corresponding to molecular absorption bands that can be used to identify the constituent components of the fluid 26. The molecular absorption bands and/or the constituent components of fluid 26 are communicated via display or the like to an operator.

It is noted that the transmission should be interrogated over a relevant spectral band, for example by sweeping the wavelength of the illuminating light source and measuring the intensity on detector 25 (FIG. 1). Tool 12 may include sensors 20a having different lengths, from microns to millimeters, of windows 32 to cover a desired range of transmission loss and sensitivity.

Refer now to FIG. 3, wherein an example of a refractive index sensor 20b is illustrated. Sensor 20b is illustrated as a Mach-Zehnder interferometer. Waveguide 40 includes a first branch 42 and a second branch 44 etched on the surface of substrate 28. Light travels along waveguide 40 in the direction indicated by the arrow. As indicated in FIG. 2, the majority of waveguide 40 is covered with overclad 36 so that the evanescent field does not penetrate into the wellbore fluid. Second branch 44 of waveguide 40 includes a window 32 in the overclad or covering to expose waveguide 44 as illustrated in FIG. 2.

The interferometric configuration of sensor 20b measures the difference in optical path length between two or more waveguides or waveguide branches. Waveguide 42 is immune to the effect of fluid on its surface, as it is covered with an optical protective layer. Second waveguide 44 has a window 32 of a specific chosen length so that the refractive index of the fluid 26 in contact with waveguide 44 alters the optical path length which is detected with the interferometric arrangement. The magnitude of the change in the optical path length can be used to assess the nature and composition of wellbore fluid 26 in contact with waveguide 44.

An example of operation is now described with reference to FIGS. 1 through 3. Light is emitted from LED source 23 and travels along optical fiber 30 protected from the downhole environment by cladding 34. When the light arrives at window 32, some of the light interacts with wellbore fluid 26, and the remaining light is reflected and travels back through the optical fiber. The reflected light travels through a Y coupler to a receiving photodiode 25 and is converted into an electrical signal. The amount of reflection depends on the refractive index of fluid 26.

From the foregoing detailed description of specific embodiments of the invention, it should be apparent that a novel and unobvious system and method for downhole testing and determination of the composition and characteristics of a wellbore fluid has been disclosed. Although specific embodiments of the invention have been disclosed herein in some detail, this has been done solely for the purposes of describing various features and aspects of the invention, and is not intended to be limiting with respect to the scope of the invention. It is contemplated that various substitutions, alterations, and/or modifications, including but not limited to those implementation variations which may have been suggested herein, may be made to the disclosed embodiments without departing from the spirit and scope of the invention as defined by the appended claims which follow.

What is claimed is:

1. An optical apparatus for investigating wellbore fluids, the apparatus comprising an optical sensor having a waveguide formed on a surface of a substrate, a portion of the waveguide being open to surrounding environment to emit an evanescent sensing field therein.

2. The apparatus of claim 1, wherein the substrate is sapphire.

3. The apparatus of claim 1, wherein the optical waveguide further includes a second waveguide portion that is coated with a protective layer such that the evanescent field does not penetrate into the surrounding environment.

4. The apparatus of claim 3, wherein the substrate is sapphire.

5. An optical system for investigating a fluid in a wellbore, the system comprising a tool suspended in a wellbore and surrounded by the fluid in the wellbore; and an optical sensor positioned on the tool, the sensor measuring at least one characteristic of the wellbore fluid,
wherein the optical sensor comprises a waveguide formed on a substrate, the waveguide having a portion open to the surrounding wellbore fluid.

6. The system of claim 5, wherein the optical sensor is a reflectance, transmission type sensor.

7. The system of claim 6, further including a second optical sensor carried by the tool, the second optical sensor being a refractive index type sensor.

8. The system of claim 7, wherein the reflectance type sensor and the refractive index type sensor are each formed on a single substrate.

9. The system of claim 8, wherein the substrate is sapphire.

10. The system of claim 5, wherein the optical sensor is a transmissive type sensor.

11. The system of claim 5, wherein the substrate is diamond.

12. The system of claim 5, wherein the substrate is sapphire.

13. The system of claim 5, wherein the optical sensor is a reflectance type sensor.

14. The system of claim 5, wherein the optical sensor is a refractive index type sensor.

15. A method of measuring the composition of a fluid in a wellbore, the method comprising the steps of:

providing a first optical sensor on a tool, the optical sensor comprising a waveguide formed on a substrate, an optically protective covering over the waveguide, and a window formed through the protective covering exposing a portion of the waveguide;
disposing the tool into a wellbore and the wellbore fluid; and
measuring at least one characteristic of the wellbore fluid.

16. The method of claim 15, wherein the substrate is sapphire.

17. The method of claim 15, wherein the first optical sensor is a reflectance type optical sensor and the tool further including a second refractive index type optical sensor.

18. The method of claim 17, wherein the second optical sensor includes a waveguide formed on the same substrate as the first optical sensor.

* * * * *